United States Patent [19]

Kessler et al.

[11] Patent Number: 4,588,586
[45] Date of Patent: * May 13, 1986

[54] METHOD FOR DISINFECTING A CONTACT LENS

[76] Inventors: Jack H. Kessler, 202 W. Newell Ave., Rutherford, N.J. 07070; Robert S. Rosenbaum, 109 Anawan Ave., West Roxbury, Mass. 02109

[*] Notice: The portion of the term of this patent subsequent to Sep. 25, 2001 has been disclaimed.

[21] Appl. No.: 621,792

[22] Filed: Jun. 18, 1984

Related U.S. Application Data

[60] Continuation-in-part of Ser. No. 455,420, Jan. 3, 1983, Pat. No. 4,473,550, which is a division of Ser. No. 225,762, Jan. 16, 1981, abandoned.

[51] Int. Cl.$^4$ .................... A61K 37/48; A61K 33/40; C12P 19/56; D06M 16/00
[52] U.S. Cl. ........................ 424/94; 424/130; 435/78; 435/264; 514/902
[58] Field of Search ............ 424/94, 50, 53, 130, 424/230, 258, 274, 317, 319, 330, 338; 435/78, 264

[56] References Cited

U.S. PATENT DOCUMENTS

| | | | |
|---|---|---|---|
| 959,605 | 5/1910 | Queisser | 424/53 |
| 2,527,686 | 10/1950 | Sandberg | 424/58 |
| 2,554,464 | 5/1951 | Krans | 424/53 |
| 3,829,329 | 8/1974 | O'Driscoll et al. | 424/130 |
| 4,150,113 | 4/1979 | Hoogendoorn et al. | 424/50 |
| 4,154,815 | 5/1979 | Pader | 424/50 |
| 4,178,362 | 12/1979 | Hoogendoorn et al. | 424/50 |
| 4,269,822 | 5/1981 | Pellico et al. | 424/50 |

OTHER PUBLICATIONS

"Enzymes"-Dixon et al.-*Academic Press Inc.*, N. Y.-1958, pp. 100-104 & 208.
Elliott-KAC: Oxidations Catalysed by Horseradish & Milk Peroxidases, Biochem. J. 26, 1281-1290 (1932).
Sizer, I. W.-The Oxidative Inactivation of Poison Ivy Allergens by Peroxidase: J. Invest. Dermatology, 16, 103-110 (1951).
Wennstrom et al.-Effect of Hydrogen Peroxide on Developing Plaque and Gingivitis in Man: *J. Clinical Period.*, 6, 115-130 (1979).

*Primary Examiner*—Douglas W. Robinson

[57] ABSTRACT

The method comprises forming a bactericide having a limited period of bacteriological activity with the bactericide comprising three components including a peroxide, a peroxidase and a source of donor molecules adopted to act as a substrate for the peroxidase; storing the three components in a nonreacting state to maintain the bactericide inactive and admixing the three components in a liquid carrier to cause a catalyzed reaction by said peroxidase for generating free radicals from the source of donor molecules and immersing the contact lens into the solution simultaneously with the admixture. The concentration level of the three components should be selected such that a substantial portion of the peroxide is consumed during the catalyzed reaction.

11 Claims, No Drawings

METHOD FOR DISINFECTING A CONTACT LENS

This application is a continuation-in-part of application Ser. No. 455,420 filed Jan. 3, 1983 now U.S. Pat. No. 4,473,550 which in turn is a division of application Ser. No. 225,762 filed on Jan. 16, 1981 and now abandoned.

This invention relates to a method of disinfecting a contact lens without applying heat.

BACKGROUND

FDA regulations requires that a contact lens be sterilized upon removal from an eye and before replacement in an eye. Soft contact lenses may be sterilized by one of two methods. The first method is the use of heat sterilization. Heat sterilization consists of boiling soft contact lenses in a saline solution for a period of about 45–50 minutes. The wearer may then remove the lens directly from the saline environment and place the contact lens in the eye.

Cold sterilization consists of disinfecting the contact lens in the absence of heat using a sterilizing solution containing a disinfectant which chemically sterilizes the contact lens. Commercially available cold sterilization systems for contact lenses have two major problems: they irritate the eye to some extent and they require an inconvenient amount of time to work, usually about four hours. The most commonly used active component of cold sterilization systems today is chlorhexidine which can be toxic and irritating to the user even after rinsing the lens.

The art has long sought a method of disinfecting a contact lens in the absence of heat; a method not based on the use of chlorhexidine; a method which is non-toxic and non-irritating to the eye; a method which will use a single solution; a method which works rapidly; a method simple to use; a method easy to convey; a method easy to store.

Hydrogen peroxide has been used in the past for disinfecting contact lenses but has been largely discarded because of the irritation it causes to the eye. This irritation is due to the high concentration of hydrogen peroxide required to be even minimally effective. We believe that high concentrations of hydrogen peroxide are required in conventional systems due to the slow rate at which bactericidal components are generated from hydrogen peroxide. The present invention uses a catalyzed system supplied in powder or pill form which continuously generates bactericidal free radicals over a controlled time period when dissolved in an aqueous carrier.

The present invention uses a peroxide based system in a non-reacting dry state which is activated by the user to form a bactericide having a limited period of bacteriological activity with the bactericide including a peroxide, a peroxidase and a source of donor molecules capable of acting as a substrate for the peroxidase. The present invention overcomes the most obvious objection to the use of hydrogen peroxide alone since the concentration of peroxide in this system is several orders of magnitude less than that used in the prior art and careful formulation of the proportion of the components of the bactericide results in the consumption of a substantial percentage of the peroxide initially exposed to the lens. The present invention results in a concentration of peroxide so low as to cause no irritation to the eye and therefore suits the criteria of an ideal clinical product.

Hydrogen peroxide dissociates into free radicals which are known to be bactericidal. The rate at which free radical species are generated from the uncatalyzed decomposition of hydrogen peroxide determines the bactericidal efficacy of this compound. Enzyme catalyzed reactions are known to occur $10^{10}$ to $10^{15}$ times as rapidly as the corresponding non-enzymatic reactions. In accordance with the present invention an enzyme, peroxidase, has been selected to catalyze the reduction of hydrogen peroxide for generating free radicals. The enzyme peroxidase catalyzes the transfer of electrons from donor molecules to acceptor molecules, peroxides. When an electron is removed from a donor molecule, this molecule is transformed into a bactericidal free radical. The free radicals generated in this process are generated at greatly elevated rates relative to the rate at which free radicals are generated from the non-enzymatic dissociation of peroxide. The present invention allows for the sterilization of a contact lens in minutes instead of hours and therefore better suits the criteria of an ideal clinical product.

Peroxidases are classified as enzymes which act to reduce hydrogen peroxide. The different types of peroxidases are distinguished by the donor molecules they use; donor molecules supply electrons which peroxidase donates to hydrogen peroxide. In accordance with the present invention a peroxidase is used to generate free radicals from donor molecules. The donor molecules must be capable of acting as a substrate for peroxidase in generating such free radicals. The method of the present invention teaches a practical means to control the generation of free radical species from a bactericide having a limited period of bacteriological activity. The bactericide of the present invention is formed by combining three components, viz., a peroxide, a peroxidase and a source of donor molecules. The bactericide will continuously generate free radicals over a defined period of time depending upon the concentration level of each component in the bactericide.

The duration of free radical production and the amount of free radicals produced can be controlled by careful formulation of the three components comprising the system. As long as the enzymatic reduction of hydrogen peroxide continues, free radicals will be generated. The free radicals being generated have an extremely short lifetime and as such must be continuously generated to prolong the period of bacteriological activity. The duration of the reaction, and therefore it bactericidal lifetime, is controlled via the formulation. Other factors remaining constant, the longer the reaction occurs the greater the bactericidal effectiveness.

The method of the present invention teaches how to maintain the bactericide in a nonreacting state; how to activate the bactericide at the critical moment when sterilization of the contact lens is desired and how to control the generation of free radicals over a preselected time period to complete the sterilization of the lens using a minimum concentration of each component so as not to result in eye irritation. Integral to the success of the invention is the subject of patient compliance in the use of the invention. Given a product which requires admixture of several components at different concentrations, it is assumed by industry that patient compliance and therefore successful use of such a product will be low. Therefore, of critical importance to the present invention is storage of the bactericide in a nonreacting state and preferably in powder or pill form so as to activate the bactericide in a liquid carrier simultaneously with the immersion on the contact lens. Inherent in the powder or pill composition is ease of storage, ease of use and a high level of patient compliance which suit the criteria for an ideal clinical product. In fact, it is only via the formulation of these components in a powder or pill which allows feasibility of this approach for contact lens sterilzation.

The concentration and nature of donor molecules in the bactericide is of paramount importance since the donor molecules or products thereof are transformed in the reaction into the bactericidal agents; the reaction of the donor molecules with the enzyme is the slowest step in the reaction mechanism. Many donor molecules may be used either alone or in combination with other donor molecules. Some donor molecules are preferred substrates relative to the type of peroxidase selected, and within such a group of donor molecules some are preferred due to interactions that donor molecules may have with bacteria or the surrounding matrix which will enhance or detract from their bactericidal activity. Some donor molecules will be effective against only a limited number of bacterial strains while other donor molecules will exert broader bactericidal efficacy. Some donor molecules will be effective against only comparatively low concentrations of bacteria while other donor molecules will exert bactericidal action over a large range of bacterial concentrations.

The present invention incorporates a peroxide, a peroxidase, and donor molecules which are readily available, inexpensive and easily incorporated into a powder or pill form and therefore suits the criteria of an ideal clinical product. It has been discovered in accordance with the present invention that a minimum concentration level of donor molecules exists below which the bactericide is ineffective for disinfecting a contact lens i.e., the rate of free radical production is too low to be characterized as having any noticeable bactericidal effectiveness. This minimum level for the donor molecule is at least $1.0 \times 10^{-7}$ molar. The minimum amount of peroxidase to achieve noticeable bactericidal effectiveness is $0.38 \times 10^{-3}$ units per ml; for hydrogen peroxide the minimum concentration level to achieve noticeable bactericidal effectiveness is $1 \times 10^{-7}$ molar.

The minimum concentration levels for effective bactericidal action are critically important to the invention since a critical aspect of sterilization solutions is the irritation caused to certain users. Hydrogen peroxide is recognized to be an eye irritant. The level of peroxide left exposed to the lens after the reaction has occurred can be controlled by carefully selecting the initial concentration of the three components and the time for which the reaction will occur. It is important to this invention that the concentrations of the three components be carefully selected to cause most of the peroxide initially exposed to the contact lens to be consumed during the reaction thus reducing the possibility for irritation. That is, the components can be formulated so that the concentration of hydrogen peroxide limits the duration and rate of the generation of free radicals. When this is done it allows for a dramatic depletion of the initial concentration of hydrogen peroxide over the concentration initially exposed to the contact lens. This type of formulation is achieved by insuring that the concentration of donor molecule is large enough so that its concentration does not influence the rate of the generation of free radicals and that the concentration of peroxidase is large enough to reduce all of the hydrogen peroxide which is thermodynamically capable of being reduced. This formulation is then pseudo-first order with respect to the donor molecule and driven largely to thermodynamic equilibrium by the concentration of peroxidase.

In general the preparation used for cold sterilization of contact lenses should have maximum concentration levels of about 0.1 milligram per ml for the enzyme, 0.1 milligram per ml for the donor molecule and 0.03% for hydrogen peroxide.

SUMMARY OF THE INVENTION

The present invention provides a practical method for producing bactericidal free radicals for disinfecting contact lens over a controlled time period by subjecting the contact lens to a mixture containing a peroxidase, a peroxide and a source of preselected donor molecules with the components formulated within predetermined concentration levels to cause a substantial proportion of the peroxide to be consumed within such time period. The three components of this invention must be stored in a nonreacting state preferably as a powder or pill until use.

According to the invention bactericidal free radicals are continuously generated in a short time period at an effective concentration by dissolving a combination of a peroxidase a peroxide and preselected donor molecules in a liquid to rapidly and efficiently form bactericidal free radicals. The components of this invention are maintained in a nonreactive state by storing the components in a powdered or pilled form and the activated by admixture in a suitable liquid carrier for use. The components of this material are compatible with common dessicants such as silica gel which might be used to prolong the shelf-life of a powdered mixture of a pill. A hermetically sealed container could alternately be used to prolong the shelf-life when extended product lifetime is necessary.

DESCRIPTION OF THE PREFERRED EMBODIMENT

The material used as a bactericide in accordance with the method of this invention is a combination of preselected donor molecules, a peroxide and a peroxidase stored in a nonreactive state such as in pill or powder form which in activated to generate bactericidal free radicals when combined to permit a catalyzed reaction by said peroxidase preferably by admixture in a suitable liquid carrier such as a buffered normal saline solution.

The components may be rendered nonreactive by using a lyophilized peroxidase, a solid donor molecule and a salt or other dry source of a suitable peroxide. Any solid entity which liberates a peroxide upon dissolution which is useable by peroxidase can serve as the source of peroxide. Sodium perborate or an organic derivative of hydrogen peroxide could serve as the source of peroxide in this invention. When this is done, all components can be mixed together and activated by introduction into a liquid carrier such as a mildly buffered aqueous saline solution. This system is compatable numerous different types of buffers which allows for a formulation organoleptically compatible with the eye.

The system of this invention incorporates a peroxide as an acceptor molecule. The enzyme peroxidase catalyzes transfer of electrons from donor molecules to acceptor molecules. When an electron is removed from the donor molecule, this molecule is transformed into a bactericidal free radical. A cycle of the enzyme mechanism is illustrated below:

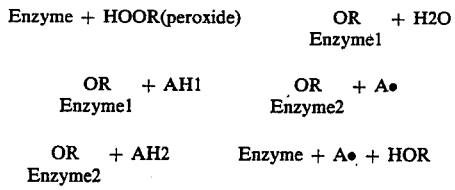

where
R=hydrogen, methyl or ethyl
AH=donor molecule
A·=free radical of donor molecule The increased rate of formation of free radicals produced by this chemical system allows for rapid generation of high concentrations of bactericidal free radicals relative to the noncatalyzed decomposition of hydrogen peroxide.

The peroxide in this invention is a material or materials which form hydrogen peroxide upon dissolution in a suitable carrier. Sodium peroxide, sodium perborate or other salts of hydrogen peroxide can readily serve as the source of peroxide for this invention since these compounds form hydrogen peroxide upon dissolution. Other peroxides like methyl peroxide and ethyl peroxide can serve as substrate for peroxidase. When compounds which generate peroxides other than hydrogen peroxide are used the cost is increased and no added advantage is obtained. Any compound which generates a peroxide that peroxidase can use to oxidize donor molecules is an acceptable source of peroxide for this invention; this includes a large number of compounds as one skilled in the art will recognize. Likewise the organic molecule 1,1-bis-1,4-diazabicyclo[2.2.2.]octane peroxide generates hydrogen peroxide upon dissolution in water and is an acceptable source of peroxide for this invention. Any compound or combination of compounds that generate a peroxide upon dissolution in water which peroxidase can use for its enzymatic reaction with donor molecules is a suitable source of peroxide for this invention.

The preferred peroxidase is horse radish peroxidase identified by the IUB and IUPAC, Enzyme Commission identification No. E.C. 1.11.1.7. Peroxidase can be obtained from a wide variety of sources; although other peroxidases, like myeloperoxidase and lactoperoxidase, can be used the cost is increased and the stability of the final product is reduced. Commercially obtained peroxidase comes lyophilized as a dry powder. Peroxidase, which uses a peroxide as an acceptor molecule, imparts to the bactericidal composition of this invention an enormous catalytic advantage in generating active constituents capable of killing selected bacteria in defined areas relative to using only hydrogen peroxide. A high concentration of free radicals are produced in short time periods for example, the reaction rate to form free radicals occurs essentially instantaneously and proceeds at a rate determined by the initial concentration of each of the three critical components of the system and the environment in which the reaction occurs. The peroxidase can come from a variety of sources and can be isolated by any of the well-known prior art procedures as used by the many companies which offer a peroxidase for sale. The use of horseradish peroxidase is preferred since it is easily isolated, has low cost, and has very high stability giving it a long lifetime; however, other sources of peroxidase can be used. Peroxidases have variable substrate specificities depending upon the source from which they are isolated. Hydrogen peroxide is often the most effective substrate.

The donor molecules are molecules which can be acted upon to aid in formation of bactericidal free radicals. Many donor molecules can be use as will be recognized by those skilled in the art. The general substrate specificity of peroxidases is such that they can use phenols, aryl and alkyl amines, hydroquinones, NADH, NADPH, palmitate, halogens, glutathione, ferrocytochrome c and ascorbate as donor molecules. This broad enzymatic substrate specificity allows for a large choice of a single donor molecule or a combination of several. Different donor molecules have different abilities and reactivities and can be selected to focus bactericidal selectivity on any given preparation by careful selection of donor molecules or by designing specific donor molecules with high selectivity for specific bacteria. We have observed that certain donor molecules are effective at high levels of bacteria (1 million/ml) while others are only effective at very low levels of bacteria. The following compounds have been found to be effective as donor molecules: ascorbic acid, tyrosine, phenylalanine, benzoic acid, salicylic acid, hydroquinone, dehydrophenylalanine, vanillan and iodide salts like sodium iodide.

Typically the number of bacteria on a contact lens after one day of wear is between 20 and 100; regulatory requirements can necessitate a formulation of this invention that is bactericidal to an environment which contains many orders of magnitude more bacteria than that found on a contact lens after a typical day of use. When formulating the invention to kill large numbers of bacteria there are certain donor molecules which are more effective than others. If an environment contains a high concentration of a bacteria which secretes an active catalase then this enzyme will compete for the hydrogen peroxide present in the formulation and reduce the effectiveness of the invention. It is therefore necessary to know something about the environment of the contact lens which is to be sterilized in order to formulate the invention properly.

A prerequisite for the storage of any preparation is not allowing all three components (donor molecules, acceptor molecules, and peroxidase) of the system to combine under conditions where the catalytic process can occur. That is, it is imperitive that the storage of the components will not allow the depletion of the component parts of the system until the reaction is initiated immediately prior to its use. If the components are allowed to react before intended for use, the combination of these components under such conditions will precipitate the depletion of the enzyme's substrate molecules and thereby attenuate the effectiveness of the preparation. Any combination of the components of this system (donor molecules, acceptor molecules, or peroxidase) which precludes the catalytic reaction from occurring is acceptable for storage prior to use. That is, if it is practical to separate any one of the three components from the other two prior to administration, this would serve the purpose of preserving the integrity of the system. Alternately it is possible to have two separate mixtures which contain any two of the components of the system in any combination and to combine these two mixtures prior to use. The present invention accomplishes this by combining the three components of the invention in a dry form.

The present invention can utilize a concentration of peroxide, preferably hydrogen peroxide, ranging from 1 millimolar to to 1 micromolar with a preferred concentration range between 0.1 millimolar and 0.001 millimolar. The present invention can utilize concentrations of donor molecules ranging from 100 millimolar to 10 micromolar with a preferred range of 35 micromolar to 10 millimolar. The present invention can utilize a concentration range of horseradish peroxidase from 0.00001 mg/ml to 1 mg/ml with a preferred range of 0.5 to 0.01 mg/ml.

EXAMPLES

EXAMPLE 1

Four patients used vials containing 0.09 mg sodium peroxide, 20 mg NaCl, 0.12 mg L-tyrosine and 5 units of HRP. To sterilize their contacts patients placed their contact lens in the vial containing these components and added 10 ml of distilled water. The contents were gently mixed and exposed to the contact lens for 3 to 5 minutes. The lens was then removed from the vial and rinsed in distilled water. There was no clinical discomfort or danger to any of the patients in this study.

EXAMPLE 2

A contact lens was exposed to ten ml of normal saline containing 0.09 mg sodium peroxide, 20 mg NaCl, 0.12 mg L-tyrosine and 5 units of HRP for several 10–15 minute sterilization cycles at room temperature. To determine if there were any deleterious effects to the lens electron micrographs were taken and the surface morphology of this lens was compared to a lens a patient had sterilized in saline with a commercially available chlorhexidine methodology; there was no difference between the two in terms of the polymer's structure.

EXAMPLE 3

After a day of wear, a Wesley-Jensen Dura-Soft lens was divided into four equal sections. One section was plated (5% sheep-blood agar) out directly. One section was immersed in $5 \times 10^{-5}$ molar peroxide for 5 minutes and then plated out. One section was sterilized using a standard Bausch & Lomb heat sterilizer and then plated out. One section was treated with $5 \times 10^{-5}$ molar peroxide, $1 \times 10^{-4}$ molar tyrosine and $2.5 \times 10^{-6}$ molar HRP (all components in 0.010 molar sodium phosphate, 0.15 molar NaCl, pH 6.8 ) for 5 minutes and then plated out. All lens sections were sterilized at room temperature with the exception of the Bausch & Lomb heat sterilizer. The plates were grown for 5 days at 37° C. and then counted. The only plates which did not have growth were from the contacts sterilized with heat and the contact sterilized in accordance with this invention.

EXAMPLE 4

A contact was contaminated with a pure hospital culture of S. aureus, exposed to a ten ml of normal saline containing 0.09 mg sodium peroxide, 20 mg NaCl, 0.12 mg L-tyrosine and 5 units of HRP for five minutes at room temperature and then plated out by the above procedure; no growth was observed.

EXAMPLE 5

1.0 ml of buffer, sodium phosphate pH 7.0, 0.10 molar was pipetted into two $10 \times 75$ mm test tubes. A loop was flamed and inserted into the buffer of one of the two test tubes, a colony of Staph. aureus cells was removed from a pure slant and placed into the liquid of one of these two test tubes. This test tube was shaken to evenly suspend the cells and then placed in a clinical centrifuge to spin at 3 to 4 thousand rpm.

70 Microliters of potassium iodide, 1.0 millimolar, was pipetted into each of the test tubes to be used. 70 microliters of 0.10 molar sodium phosphate, pH 7.0 was pipetted into each of the test tubes to be used. The centrifuge containing the Staph. cells was stopped and the supernatant was poured off; the Staph. cells were resuspended in phosphate buffer, 1.0 ml, and spun in the centrifuge again at 3 to 4 thousand rpm.

Hydrogen peroxide, 1.0 millimolar was diluted serially by factors of ten to a concentration of 100 nanomolar; 20 microliters of the serial dilution of hydrogen peroxide were added to individual test tubes containing both 70 microliters of phosphate buffer and potassium iodide. The centrifuge containing the Staph. cells was stopped and the supernatant was poured off; the Staph. cells were resuspended in phosphate buffer, 1.0 ml, and spun in the centrifuge again at 3 to 4 thousand rpm.

Horse radish peroxidase was weighed out and dissolved in phosphate buffer to a concentration of 0.5 mg per ml. The centrifuge was stopped and the supernatant of the test tube containing the Staph. cells was poured off. The cells were suspended in 1.0 ml of phosphate buffer and their optical density was measured in a Gilford spectrophotometer at 600 nm. The optical density was recorded and the cell suspension was diluted until the optical density was 0.05 OD. After this was done 20 microliters of this suspension of cells was added to each test tube.

20 Microliters of the solution of horse radish peroxidase was added to each test tube and the test tubes were gently shaken. The test tubes were allowed to incubate for 45 minutes at 37 degrees centigrade. After the incubation time 1.0 ml of phosphate buffer was pipetted into a test tube. A calibrated loop was flamed placed into the test tube. A plate of 5%-sheep blood agar was streaked for each test tube in the experiment. The colonies on each plate were counted and compared to control plates which had not received peroxidase, positive control, or cells, negative control.

The positive control had over 100 colonies on its surface, the negative control had no colonies on its surface, all plates with a final concentration of hydrogen peroxide in the test solution greater than or equal to 1 micromolar had no colonies on their surface.

EXAMPLE 6

The protocol of example 5 was followed except that serial dilutions of horse radish peroxidase and hydrogen peroxide were made, the enzymatic reaction was allowed to proceed only for five minutes at room temperature before being plated out and 1 million bacteria per ml of S. aureus were used in the assay. The minimum concentration of hydrogen peroxide that was necessary to kill all the bacteria was $10^{-5}$M in the final reaction. the minimum concentration of enzyme (Sigma 150 units/mg) necessary to kill all bacteria present was 0.010 mg/ml.

EXAMPLE 7

The protocol of experiment 5 was followed except that the hydrogen peroxide concentration and horse radish peroxidase concentration were kept at 0.10 millimolar and 0.25 mg/ml (150 units/mg). The concentration of potassium iodide was serially diluted by factors of ten. The minimum concentration of potassium iodide necessary to insure complete bactericidal action was 35 micromolar.

We claim:

1. A method for disinfecting a contact lens comprising forming a bactericide having a limited period of bacteriological activity, said bactericide comprising a source of peroxide, a peroxidase within the classification E.C. 1.11.1-7 and a source of predetermined donor molecules adapted to act as a substrate for said peroxidase, storing said three components in a nonreacting state such that said bactericide is inactive; admixing the three components in a liquid carrier to cause a catalyzed reaction by said peroxidase for generating free radicals from said source of donor molecules; selecting the concentration level of said three components such that a substantial percentage of said peroxide is consumed during said catalyzed reaction; and immersing the contact lens into said solution substantially simultaneous with the admixture of all three components whereby bacteria present on said contact lens will be killed during said limited period of bacteriological activity.

2. A method as defined in claim 1 wherein said components are stored in a dry form such as a powder or a pill needing only to be dissolved in a suitable liquid carrier to be activated.

3. A method as defined in claim 1 wherein said source of donor molecule is selected from the class consisting of iodide salts, tyrosine, phenylalanine, benzoic acid, dehydrophenylalanine and vanillin.

4. A method as defined in claim 3 wherein the concentration of said donor molecule is in a concentration range from 10 micromolar to 100 millimolar.

5. A method as defined in claim 4 wherein said source of peroxide is selected from the group consisting of hydrogen peroxide, sodium perborate, methyl peroxide, ethyl peroxide and 1,1-bis-1,4-diazabicyclo2.2.2 octane peroxide.

6. A method as defined in claim 5 wherein said peroxide concentration is in a range of between 1 millimolar to 1 micromolar.

7. A method as defined in claim 6 wherein said source of peroxidase is horseradish peroxidase.

8. A method as defined in claim 7 wherein the concentration of said peroxidase is in a range between 0.00001 and 1.0 mg/ml.

9. A method as defined in claim 2,4 or 8 wherein said source of donor molecules is a salt of iodide.

10. A method as defined in claim 9 wherein said liquid carrier comprises water or a saline solution.

11. A method as defined in claim 4 wherein said source of peroxide is sodium perborate.

* * * * *